United States Patent [19]

Beck et al.

[11] 4,021,443

[45] May 3, 1977

[54] PERCHLORODIAZAFULVENE

[75] Inventors: Gunther Beck, Leverkusen; Fritz Döring, Odenthal-Gloebusch; Helmut Heitzer, Opladen; Hans Holtschmidt, Bergisch-Gladbach-Kalmuenten, all of Germany

[73] Assignee: Bayer Aktiengesellschaft, Leverkusen, Germany

[22] Filed: Oct. 29, 1975

[21] Appl. No.: 627,154

[30] Foreign Application Priority Data

Nov. 15, 1974 Germany .......................... 2454326

[52] U.S. Cl. ................................. 260/309; 424/273
[51] Int. Cl.² ...................................... C07D 233/68
[58] Field of Search ........................ 260/309, 653.5

[56] References Cited

UNITED STATES PATENTS

| | | | |
|---|---|---|---|
| 2,754,336 | 7/1956 | Chernosky et al. | 260/653.5 |
| 3,501,286 | 3/1970 | Draber et al. | 260/309 |
| 3,631,058 | 12/1971 | Beck et al. | 260/309 |
| 3,697,608 | 10/1972 | Bellis | 260/653.5 |

FOREIGN PATENTS OR APPLICATIONS

| | | | |
|---|---|---|---|
| 2,234,981 | 2/1973 | Germany | 260/309 |
| 709,887 | 6/1954 | United Kingdom | 260/653.5 |

OTHER PUBLICATIONS

Buehler et al. Survey of Organic Syntheses p. 80 N.Y., Wiley-Interscience, 1970.
Fieser et al. Reagents for Organic Synthesis vol. 1, p. 1281, N.Y., Wiley, 1967.
Kurginyan et al. Chem. Abst. 1975, vol. 82, No. 139177z.
Nozaki et al. Chem. Abst. 1969, vol. 71, No. 80826c.
Sonn et al. Chem. Abst. 1924, vol. 18, pp. 3059–3060.

*Primary Examiner*—Natalie Trousof
*Attorney, Agent, or Firm*—Burgess, Dinklage & Sprung

[57] ABSTRACT

Perchlorodiazafulvene having the formula

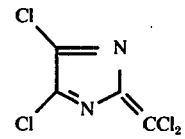

is prepared by reacting 2,4,5-trichloro-2-trichloromethyl-2H-imidazole having the formula

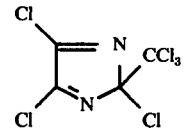

with dechlorinating agents at elevated temperatures and is useful as a fungicide.

1 Claim, No Drawings

PERCHLORODIAZAFULVENE example using phosphorus or sulphur as dechlorinating agents:

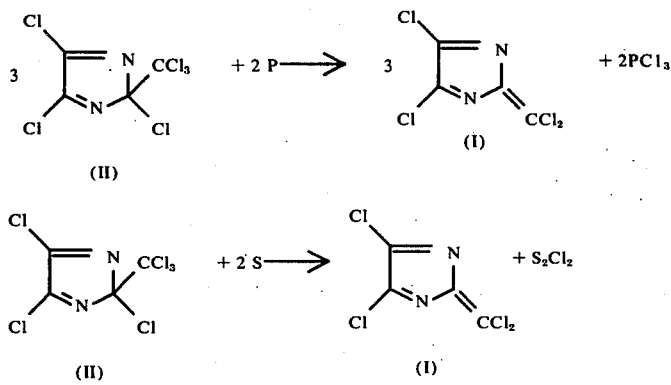

SUMMARY

This invention relates to a perchlorodiazafulvene, which is new, and to a process for its preparation.

It has been found that perchlorodiazafulvene of the formula

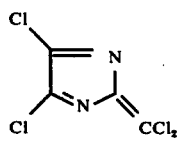

is obtained when 2,4,5-trichloro-2-trichloromethyl-2 H-imidazole of the formula

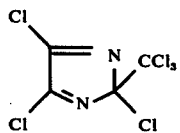

is reacted with dechlorinating agents at an elevated temperature.

In general, the reaction is carried out in a temperature range of 50° to 250° C, preferably between 100° and 220° C.

DESCRIPTION

The following may be mentioned as examples of dechlorinating agents: zinc, iron, phosphorus, sulphur and metal salts, preferably chlorides, in which the metal is in the lower of at least two possible oxidation levels, for example copper (I) chloride or tin (II) chloride. Phosphorus, sulphur, copper (I) chloride and zinc are preferred. Phosphorus is particularly preferred. Of the various modifications of phosphorus, both white and red phosphorus are suitable. Because white phosphorus is more difficult to handle, due to its high toxicity and its ready inflammability, red phosphorus is as a rule particularly preferred.

The molar ratio of the dechlorinating agent used to the starting material is generally in the range from 0.2 to 4, preferably 0.3 to 3.

The equations which follow are intended further to illustrate the process according to the invention, for example using phosphorus or sulphur as dechlorinating agents:

In the case of phosphorus being used as the dechlorinating agent for the reaction according to the process of the invention, ⅔ mol of phosphorus is required per mol of starting compound (II). Hence, in the process of the invention, preferably at least the stoichiometrically required amount, that is to say ⅔ mol in this case, is employed per mol of starting compount (II). Of course, it is also possible to use less than an equivalent amount of dechlorinating agent. In that case, the unconverted starting material (II) can be separated from the reaction product (I) in accordance with the customary methods (fractional vacuum distillation using a column and/or fractional crystallisation, for example from petroleum ether and/or by chromatographic methods) and can, if desired, be used for a further reaction.

In some cases it has also proved suitable to carry out the process according to the invention in the presence of a diluent which is inert towards the reactants. Examples of diluents which may be mentioned are ethers such as dioxane and tetrahydrofurane, and also 1,2,4-trichlorobenzene, naphthalene, methylnaphthalene, acenaphthylene, diphenyl or phosphorus tribromide. The function of a diluent can however also, for example in the case of non-metallic dechlorinating agents such as phosphorus or sulphur, be assumed by the liquid chlorides $PCl_3$ or $S_2Cl_2$ which arise as reaction products.

2,4,5-Trichloro-2-trichloromethyl-2H-imidazole of the formula (II) used as the starting material, obtained when the known 2-methylimidazole (III), in an inert diluent, is first converted to the hydrochloride by reaction with hydrogen chloride, and the hydrochloride is subjected to a chlorination by reaction with elementary chlorine. The equation which follows is intended to explain the reaction in more detail:

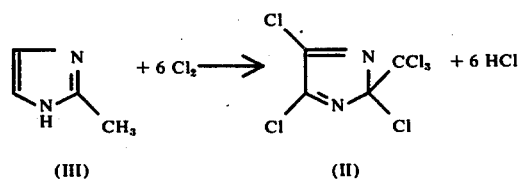

In principle, suitable inert diluents are all solvents which are resistant to chlorine, for example chlorinated aliphatic and aromatic hydrocarbons, such as chloroform, carbon tetrachloride, 1,1,2,2-tetrachloroethane, tetrachloroethylene, 1,1,2,3,3-pentachloropropane and 1,2,4-trichlorobenzene as well as phosphorus oxychloride.

However, of this range, those inert diluents are particularly preferred which have the property — which is extremely valuable for carrying out the chlorination in practice — of exhibiting marked solvent power for the hydrochloride of (III), especially in the presence of excess dissolved hydrogen chloride. Examples which may be mentioned are phosphorus oxychloride, chloroform and 1,1,2,2-tetrachloroethane. If, for example, hydrogen chloride is passed into a mixture of (III) and phosphorus oxychloride or 1,1,2,2-tetrachloroethane whilst cooling at room temperature, the hydrochloride of (III) precipitates in the first instance, but redissolves on further saturation of the suspension with HCl. If chloroform is used as the diluent, then (for example at a dilution of about 5 millilitres of chloroform per gram of (III)) there is, even from the start, no observable separation of a hydrochloride precipitate on corresponding conversion of (III) with HCl. Accordingly, the preparation of (II) is carried out particularly preferentially by mixing (III) with one of the particularly preferred diluents mentioned and passing HCl gas into the mixture at room temperature (appropriately whilst cooling), until the precipitate which may have separated out has redissolved, after which the chlorination is started in the homogeneous phase. Since further quantities of HCl are produced during the chlorination it even suffices only to pass hydrogen chloride into the mixture initially until no further exothermic reaction is detectable and then to chlorinate the suspension which has undergone partial solution.

The particular advantages of a chlorination reaction carried out in this way are:

1. A low ratio of diluent to (III) (1 to 10, preferably 2 to 5, parts by volume of particularly preferred diluent per gram of (III)).
2. Naturally, a lower time requirement than in the case of chlorination in the heterogeneous phase.
3. High yields (mostly about 90% of theory).
4. No by-products. The purities determined by gas chromatography are in every case about 99%.

After the HCl treatment of (III), which has been described, has been carried out, chlorination is initially carried out approximately at room temperature. The amount of chlorine used over the entire course of the chlorination to give (II) is always so chosen, to achieve as rapid and complete aconversion as possible, that a greenish coloration of the gas which leaves the apparatus indicates a slight excess. The temperature is raised gradually (suitably it is always raised only when an exothermic phase has subsided) until a temperature range of about 50° to 150° C is reached. This final range depends on the particularly preferred diluent employed. Phosphorus oxychloride and chloroform are at the lower limit and 1,1,2,2-tetrachloroethane at the upper limit. Of course, chlorinations in $POCl_3$ or in $CHCl_3$ can also be carried out above the reflux temperature by stripping off the diluent in vacuo and continuing the chlorination until the desired temperaure is reached or by distilling off the diluent in the stream of chlorine in the course of raising the temperature. After completion of the chlorination, the mixture is, if desired, distilled in vacuo and/or recrystallised, for example, from petroleum ether.

To carry out the process according to the invention it is possible, for example, to mix the starting compound of the formula (II) with, preferably, between the stoichiometrically required amount and twice the stoichiometrically required amount of dechlorinating agent and heat the mixture, if appropriate in an inert gas atmosphere (for example nitrogen or argon) to 50°–250° C, preferably to 100°–220° C. The progress of the reaction or the degree of conversion can be determined by gaschromatographic analysis. An altenative procedure is to take initially the starting material (II) together with a minor portion of the dechlorinating agent, in a temperature range in which the reaction does not take place too slowly, for example between 150° and 180° C, and to add the main part of the dechlorinating agent progressively in small portions.

Where phosphorus or sulphur is used as the dechlorinating agent, the chlorides $PCl_3$ or $S_2Cl_2$ produced as reaction products can either be distilled off directly in order thus to be able to remain at the desired higher temperature, or the reaction can be carried out in an apparatus fitted with a reflux condenser. In that case, the temperaure of the reaction mixture drops from an initial value of 170°–180° C (in the case of red phosphorus) or 200°–210° C (in the case of sulphur) as long as $PCl_3$ (boiling point: 74.5° C) or $S_2Cl_2$ (boiling point: 137° C) are still being formed, and this drop can be used to detect the end point of the process according to the invention.

It is true that longer reaction times and working in the upper part of the preferred temperature range naturally favours the conversion of (II) to (I); on the other hand, under these conditions the perchlorodiazafulvene (I) itself starts to react to give undesired residues which can no longer be distilled so that it can be advantageous to discontinue the reaction of (II) to give (I) when the conversion is incomplete.

The reaction mixtures obtained in accordance with the process of the invention can be worked up in the usual ways, preferably by vacuum distillation. It can be expedient first to remove residues, for example excess dechlorinaing agents, metal chlorides formed and the like, by dissolving out the desired reaction product and any uncoverted starting material, for example by means of carbon tetrachloride or benzene. The separation of (I) and any re-isolated (II) can, as already mentioned, be effected in accordance with generally customary methods.

It must be regarded as extremely surprising that it should prove possible at all to isolate a fulvene derivative (I), with three conjugated double bonds, at the high dechlorination temperatures.

The perchlorodiazafulvene according to the invention is new and useful as a fungicide. (See Example 8 herein)

The following Examples illustrate the invention.

EXAMPLE 1

To a mixture of 867 g (3 mols) of fused 2,4,5-trichloro-2-trichloromethyl-2 H-imidazole and 20 g of finely powered red phosphorus, in a three-necked flask equipped with a stirrer, reflux condenser and thermometer, are added, in portions, a further 104 g of red phosphorus (making a total of 124 g corresponding to 4 mols) over the course of about 2 hours at about 170° C, with exclusion of moisture; in the course of the addition, the reaction temperature drops to about 130° C as a result of the progressively formed phosphorus trichloride. The mixture is then additionally heated for 30 hours under reflux, during which the reaction temperature drops progressively. The final temperature after 30 hours is about 105° C. After stripping off, in a water-pump vacuum, the phosphorus trichloride formed, the residue is distilled, under the vacuum from an oil pump, until the bath temperature is about 135° C. The bulk (of the product) boils at 83° C/0.8 mm Hg. Yield: 494 g (corresponding to 75.5% of theory) of perchlorodiazafulvene of the formula

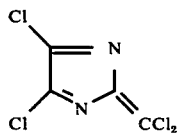

The purity determined by gas chromatography is 99.8%. Colourless crystals from petroleum ether, of melting point 75° C. The empirical formula $C_4Cl_4N_2$ is confirmed by the mass spectrum. The compound shows a characteristic IR spectrum with the following bands (in cm$^{-1}$): 1,580 st, 1,500 w, 1,250 st, 1,240 st, 1,200 m, 1,060 w, 1,040 w, 1,025 m, 965 st, 920 m, 855 st, 690 m, 590 m, 530 w and 475 w. ($st$ = strong, $m$ = medium, $w$ = weak).

The UV spectrum of the compound shows the following characteristic features (in cyclohexane):

| | |
|---|---|
| $\nu_{max_1}$ = 31,000 cm$^{-1}$, | $\epsilon_{max_1}$ = 23,950 |
| $\nu_{max_2}$ = 31,750 cm$^{-1}$, | $\epsilon_{max_2}$ = 24,100. |

2,4,5-Trichloro-2-trichloromethyl-2 H-imidazole used as the starting material, is obtained as follows:

a. A vigorous stream HCl is passed over a stirred suspension of 750 g (9.15 mols) of 2-methylimidazole in 3,000 ml of phosphorus oxychloride, whilst initially cooling with ice, until the exothermic reaction of formation of the hydrochloride has subsided and only a little additional HCl is taken up by the suspension (time required about 1 hour). Thereafter, chlorine gas is passed in, starting at room temperature, initially with slight cooling and subsequently with a slow rise in temperature. After a period of chlorination of 17 hours, a clear light yellow solution is obtained at 53° C. This is heated in a stream of chlorine, over the course of a further 6 hours, until reflux is reached (about 105° C), at which temperature the mixture is post-chlorinated for 2 hours. After stripping off the POCl$_3$ in vacuo, the residue is subjected to fractional distillation: Boiling point 96°–105° C/0.03 mm Hg; 2,479 g of 2,4,5-trichloro-2-trichloromethyl-2 H-imidazole of 99.0% purity according to gas chromatography.

Yield: 93% of theory.
Structural formula:

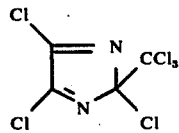

Colourless crystals from petroleum ether, of melting point 66°–68° C. The empirical formula $C_4Cl_6N_2$ is confirmed by the mass spectrum.

In a repeat experiment, a total chlorination time of only 21 hours is required for 1,000 g (12.2 mols) of 2methyl-imidazole in 3,000 ml of POCl$_3$. Yield of pure product: 95% of theory.

The compound shows a characteristic IR spectrum with the following bands (in cm$^{-1}$): 1,595 m, 1,560 st, 1,230 m, 1,085 m, 1,070 st, 970 m, 850 m, 825 st, 795 st, 745 st, 590 m and 460 w ($st$ = strong, $m$ = medium, $w$ = weak).

b. A mixture of 100 g (1.22 mols) of 2-methyl-imidazole and 500 ml of POCl$_3$ is treated with HCl gas for about 0.5 hour, as described above. Thereafter chlorination is carried out for 5.5 hours, starting at 27° C and gradually raising the temperature to 60° C, and at 60° C chlorination is continued for a further 2.5 hours, after which the suspension has been converted to a light yellow solution. The gas chromatogram of the reaction solution shows that in addition to POCl$_3$ practically exclusively the desired 2,4,5-trichloro-2-trichloromethyl-2 H-imidazole is present. After stripping off the phosphorus oxychloride, 288 g of 2,4,5-trichloro-2-trichloromethyl-2 H-imidazole, which according to analysis by gas chromatography is 98.2% pure, are obtained at 117° to 122° C/14 mm Hg. Yield: 80.4% of theory, relative to 100% pure product.

c. A vigorous stream of hydrogen chloride gas is initially passed over, and then into, a mixture of 96 g (1.17 mols) of 2-methyl-imidazole and 500 ml of POCl$_3$ whilst cooling with ice at between 10° and 20° C, whereupon a practically clear solution is obtained after 50 minutes. The mixture is brought to reflux (about 102° C) over the course of 6 hours by gradually raising the temperature, in a stream of chlorine. After cooling, POCl$_3$ is stripped off until an internal temperature of 60° C/20 mm Hg is reached and the mixture is again chlorinated for 2.5 hours, for 2 hours of which the temperature is between 150° and 160° C. Fractionation at 120°–122° C/17 mm Hg gives 307 g of distillate which, according to the gas chromatogram, represents pure 2,4,5-trichloro-2-trichloromethyl-2 H-imidazole. Yield: 90.8% of theory.

d. A vigorous stream of HCl is passed into a solution of 82 g (1 mol) of 2-methyl-imidazole in 400 ml of chloroform for about half an hour, whilst cooling at between 20° and 30° C, until the exothermic reaction has ended. In the course thereof, no temporary precipitation is observable. Thereafter chlorine is passed in, starting at 20° C, at a rate such that the greenish-coloured gas which leaves the apparatus indicates a slight excess throughout. The mixture is brought to reflux (about 60° C) over the course of about 4 hours and the temperature is then raised to 75° C over the course of a further 8 hours whilst distilling off a part of the chloroform in the stream of chlorine. Fractionation, as described above, gives 256 g (corresponding to 88.6% of theory) of 2,4,5-trichloro-2-trichloromethyl-2 H-imidazole of 99.9% purity according to gas chromatography.

e. A vigorous stream of HCl is initially passed over, and then into, a mixture of 96 g (1.17 mols) of 2-methyl-imidazole and 500 ml of 1,1,2,2-tetrachloroethane, initially whilst cooling with ice, at between 20° and 30° C, whereupon, after about 70 minutes, the precipitate which initially separated out redissolves completely. Thereafter the temperature is raised slowly so as to bring the mixture, in a stream of chlorine, to reflux (about 150° C) (which requires about 7 hours). At about 40° C, a precipitate temporarily separates out, which becomes less marked at about 80°–85° C, accompanied by strong consumption of chlorine, and dissolves completely at about 95 C. Chlorination is now continued at about 150 C until the gas chromatogram shows that the conversion to 2,4,5-trichloro-2-trichloromethyl-2 H-imidazole is as complete as possible. The isolation and yield correspond to the preceding examples.

EXAMPLE 2

A mixture of 289 g (1 mol) of 2,4,5-trichloro-2-trichloromethyl-2 H-imidazole and 41 g (4/3 mols) of red phosphorus is kept in an apparatus as described in Example 1 for 9 hours in an oil bath at a bath temperature of 180 –185 C. After this time, the internal temperature has fallen to about 120 C. After cooling, the reaction mixture is stirred with about 250 ml of carbon tetrachloride, undissolved material is filtered off whilst excluding moisture, and the filtrate is distilled in a water-pump vacuum after stripping off the PCl and the CCl . At 115 to 118 C/13 mm Hg, 152 g of distillate are obtained, containing, according to the gas chromatogram, 92.7% of perchlorodiazafulvene, identical with that from Example 1, and 4.8% of starting material. This corresponds to a yield of 66.3% of theory, relative to the conversion.

EXAMPLE 3

A mixture os 867 g (3 mols) of 2,4,5-trichloro-2-trichloromethyl-2 H-imidazole, 124 g (4 mols) of red phosphorus and 250 ml of phosphorus trichloride is kept in a three-necked flask, fitted with a stirrer, a thermometer and an approx. 60 cm long packed column with dephlegmator, in an oil bath at, initially, 155 C. Starting at an internal temperature of about 105 C, phosphorus trichloride is slowly distilled off. In the course of about 10 hours, the bath temperature is slowly raised to 170 C, in the course of which the internal temperature rises to about 140 –145 C whilst PCl constantly continues to distil off. The mixture is worked up as described in Example 1. 383 g of distillate are obtained, consisting, according to the gas chromatogram, of 97.3% of perchlorodiazafulvene, identical with that from Example 1, and 2.5% of starting mateial. This corresponds to a yield of perchlorodiazafulvene of 57.7% of theory, relative to the conversion.

EXAMPLE 4

A mixture of 867 g (3 mols) of 2,4,5-trichloro-2-trichloromethyl-2 H-imidazole, 31 g (1 mol) of red phosphorus and 250 ml of phosphorus trichloride is heated in an apparatus as described in Example 3. Over the course of about 10 hours, the internal temperature is raised to 150 C whilst constantly slowly distilling off PCl , and the mixture is then kept at this temperature for a further 8 hours. After working up analogously to Example 1, 638 g of distillate, containing 189 g of perchlorodiazafulvene identical with that from Example 1, and 409 g of starting material, are obtained. This corresponds to a yield of 54.7% of theory, relative to the conversion.

EXAMPLE 5

173.4 g (0.6 mol) of 2,4,5-trichloro-2-trichloromethyl-2 H-imidazole and 12.4 g (0.4 mol) of red phosphorus are kept for about 2 hours in a stirred apparatus with attached distillation bridge under dry nitrogen, in an oil bath at 175 to 185 C, in the course of which phosphorus trichloride formed distils off. The internal temperature, which initially is about 180 C, first drops to 155 –160 C and rises again, toward the end of the 2 hours, to about 170 C. Working up analogously to Example 1 gives 100 g of a distiallate which according to analysis by gas chromatography consists of 83.5% of perchlorodiazafulvene, identical with that from Example 1, and 16.4% of starting material. This corresponds to a yield of 70.5% of theory, relative to the conversion.

EXAMPLE 6

289 g (1 mol) of 2,4,5-trichloro-2-trichloromethyl-2H-imidazole and 32 g (1 mol) of sulphur are heated, in a stirred apparatus with attached distillation bridge, for 1.25 hours in an oil bath at 225 to 230 C, in the course of which disulphur dichloride distils off. The internal temperature rises, before the elimination of sulphur chloride starts, to about 210 C; after the reaction has started, the internal temperature drops in a few minutes to about 190 C. After stripping off the sulphur chloride, the mixture is distilled at 0.7 mm Hg up to a bath temperature of 150 C. 193 g of distillate are obtained, containing, according to analysis by gas chromatography, 46 g of perchlorodiazafulvene and 144 g of starting material. This corresponds to a yield of 42.2% of theory, relative to the conversion.

EXAMPLE 7

173.4 g (0.6 mol) of 2,4,5-trichloro-2-trichloromethyl-2-H-imidazole and 131 g (1.32 mols) of copper (I) chloride are kept for 6 hours at between 130 and 150 C — of which 4 hours are at 150 'C — in a stirred apparatus under dry nitrogen. Distillation at 0.5 mm Hg up to a bath temperature of 150 C gives 67 g of distillate which, according to the gas chromatogram, contains 31 g of perchlorodiazafulvene and 36 g of starting material. Yield 29.8% of theory, relative to the conversion.

EXAMPLE 8

Shoot Treatment Test /. Cereal Rust (Leaf-destroying mycosis)

To produce a suitable preparation of active compound, 0.25 part by weight of perchlorodiazafulvene is taken up in 25 parts of weight of dimethylformamide and 0.06 part by weight of emulsifier W and 975 parts by weight of water are added. The concentrate is diluted with water to a final concentration of 0.025% by weight of the spray liquor.

To test the protective activity, single-leaved young wheat plants of the Michigan Amber variety are inoculated with a uredospore suspension of *Puccinia recondita* in 0.1% strength aqueous agar. After the spore suspension has dried on, the wheat plants are sprayed with the preparation of active compound until dewmoist and are placed in a greenhouse at about 20 C and 100% atmospheric humidity for 24 hours, in order to incubate.

After 10 days' dwell time of the plants at a temperature of 20 C and 80–90% atmospheric hunidity, the occurence of rust pustules on the plants is evaluated. The degree of infection is expressed as a percentage of the infection of the untreated control plants. 0% denotes no infection and 100% denotes the same degree of infection as in the case of the untreated control. The active compound is the more active, the lower is the degree of rust infection.

In the present case, an infection of 25%, relative to the untreated control sample, was found at a concentration of 0.025% by weight.
What is claimed is:
1. Perchlorodiazafulvene having the formula
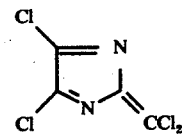

UNITED STATES PATENT AND TRADEMARK OFFICE
CERTIFICATE OF CORRECTION

PATENT NO. : 4,021,443
DATED : May 3, 1977
INVENTOR(S) : Gunther Beck et al

It is certified that error appears in the above-identified patent and that said Letters Patent are hereby corrected as shown below:

Column 5, line 35, after "stream" insert -- of --.

Column 7, line 64, and
Column 8, line 2, "1/2 hours" should read -- 2 1/4 hours --.

Column 8, line 3, "distiallate" should read -- distillate --.

Column 8, line 25, "42.2%" should read -- 42.1% --.

Column 7, line 1, "95 C" should read -- 95°C --.
        2, "150 C" should read -- 150°C --.
      13, "180-185 C" should read -- 180-185°C --.
      14, "120 C" should read -- 120°C --.
   32-33, "155 C" should read -- 155°C --.
      33, "105 C" should read -- 105°C --.
      36, "170 C" should read -- 170°C --.
      37, "140-145 C" should read -- 140-145°C --.
      52, "150 C" should read -- 150°C --.
      66, "175 to 185 C" should read -- 175 to 185°C --.
      68, "180 C" should read -- 180°C --.

Column 8, line 1, "155-160 C" should read -- 155-160°C --.
      2, "170 C" should read -- 170°C --.
     13, "225 to 230 C" should read -- 225 to 230°C --.
     16, "210 C" should read -- 210°C --.
     18, "190 C" should read -- 190°C --.
     20, "150 C" should read -- 150°C --.

UNITED STATES PATENT AND TRADEMARK OFFICE
CERTIFICATE OF CORRECTION

PATENT NO. : 4,021,443
DATED : May 3, 1977
INVENTOR(S) : Gunther Beck et al

It is certified that error appears in the above-identified patent and that said Letters Patent are hereby corrected as shown below:

Column 8, line 30-31, "130 and 150 C" should read
-- 130 and 150°C --.
31, "150 C" should read -- 150°C --.
33, "150 C" should read -- 150°C --.
56, "20 C" should read -- 20°C --.
61, "20 C" should read -- 20°C --.

Signed and Sealed this ninth Day of August 1977

[SEAL]

Attest:

RUTH C. MASON
*Attesting Officer*

C. MARSHALL DANN
*Commissioner of Patents and Trademarks*